United States Patent [19]

Atkins et al.

[11] Patent Number: 4,689,415

[45] Date of Patent: Aug. 25, 1987

[54] TRANS OCTAHYDROQUINOLINE INTERMEDIATE

[75] Inventors: Randall K. Atkins; Leland O. Weigel, both of Indianapolis, Ind.

[73] Assignee: Eli Lilly and Company, Indianapolis, Ind.

[21] Appl. No.: 826,401

[22] Filed: Feb. 5, 1986

Related U.S. Application Data

[62] Division of Ser. No. 601,753, Apr. 18, 1984, Pat. No. 4,587,351.

[51] Int. Cl.$^4$ .......................................... C07D 215/06
[52] U.S. Cl. ................................................ 546/15
[58] Field of Search ........................ 549/333; 546/15

[56] References Cited

U.S. PATENT DOCUMENTS

4,198,415  4/1980  Kornfeld et al. .................. 424/258
4,537,964  8/1985  Schaus ............................... 544/250

OTHER PUBLICATIONS

Nwaukwa et al., *Tetrahedron Letters* vol. 23, No. 1, 35 (1982).
Schneider et al., *J. Org. Chem.*, 47, 364 (1982).
Lee et al., *Tetrahedron Letters* No. 20, 1641, (1976).
Wolfe et al., *Chemical Communications*, 1420 (1970).
Stevens et al., *J. Org. Chem.*, 45, 2030 (1980).
Nwaukwa et al., *Tetrahedron Letters*, vol. 23, No. 31, 3131 (1982).
Marshall et al., *Synthetic Communications* 9(2), 123 (1979).
Meyers, *J. Org. Chem.*, vol. 26, 1046 (1961).
Sawicki, *Tetrahedron Letters*, vol. 23, No. 22, 2249 (1982).
Quici et al., *J. Org. Chem.*, vol. 44, No. 19, 3436 (1979).
Regen, *J. Org. Chem.*, vol. 42, No. 5, 875 (1977).

*Primary Examiner*—Nicky Chan
*Attorney, Agent, or Firm*—Bruce J. Barclay; Leroy Whitaker

[57] ABSTRACT

The present invention pertains to a process for preparing ketones employing a silica catalyzed oxidation of a secondary alcohol with calcium hypochlorite in acetonitrile.

1 Claim, No Drawings

TRANS OCTAHYDROQUINOLINE INTERMEDIATE

This application is a division of application Ser. No. 601,753, filed Apr. 18, 1984, now U.S. Pat. No. 4,587,351.

SUMMARY OF THE INVENTION

This invention provides a process for preparing a compound of the formula

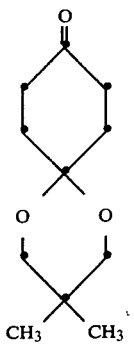

comprising reacting a secondary alcohol of the formula

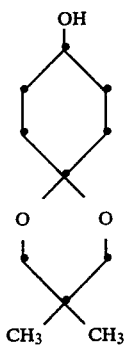

with calcium hypochlorite in acetonitrile in the presence of silica at about a temperature in the range of about 15° C. to about 35° C.

The present invention also provides trans octahydroquinoline intermediates prepared from compounds synthesized by the present process.

DETAILED DESCRIPTION OF THE INVENTION

Temperatures will be provided herein as degrees Celsius.

While applicants are not bound by any theoretical explanations of their invention, it is believed that the present invention solves the problem of prepararing highly acid labile ketones by oxidizing the corresponding alcohol, and obtains high yields of the desired ketone, by carrying out the reaction under neutral or slightly alkaline conditions. Further, the process solves the problem of isolating a water soluble product by employing aprotic reaction conditions.

The process is carried out by dissolving the starting alcohol of the formula specified above in acetonitrile. The amount of solvent used in the present process is not critical, but no more than necessary to dissolve the starting alcohol and desired product need be used. The reaction is preferably conducted in the absence of water.

Silica is used to catalyze the reaction of the alcohol to the ketone in the present process. The preferred form of silica used in the process is silica gel, a precipitated silicic acid in the form of lustrous granules. Silica gel is an amorphous form of synthetically manufactured silica which is chemically inert, non-toxic, noncorrosive and non-deliquescent. Silica gels are available commercially in a variety of mesh sizes. An economically preferred type of silica gel has a mesh size of 60 to 200 mesh based on U.S. sieve sizes. The quantity of silica employed in the process will be in the range of 0.5 to 1.2 equivalents of silica for each equivalent of starting alcohol by weight. Preferably one gram of silica will be used for each gram of starting alcohol.

Calcium hypochlorite, also known as losantin but most commonly known and used as "swimming pool bleach," is employed as the oxidizing agent in the process of the present invention. Calcium hypochlorite generally is not prepared in pure form, but is typically available as a commercial product containing at least 50%, but generally less than 75%, of available Ca(OCl)$_2$. It is a solid, non-aqueous compound. Calcium hypochlorite is employed herein at a quantity in the range of about 0.5 to about 1.5 equivalents for each equivalent of secondary alcohol by weight, more preferably one gram of calcium hypochlorite is used for each gram of starting alcohol. Large excesses of hypochlorite are not necessary nor desirable due to a tendency to create impurities.

Due to the highly acid labile nature of the molecule employed herein, the present process is preferably conducted in the presence of an unreactive base capable of acting as a buffer to the system. The term "unreactive base", as used herein, represents a base capable of stabilizing the starting alcohol and final ketone and which is essentially inert to the surroundings. Preferred unreactive bases include inorganic bases such as calcium carbonate, potassium carbonate, sodium carbonate and especially sodium bicarbonate. A sufficient amount of base should be employed herein so as to maintain the reaction medium at a neutral or slightly basic pH.

The requirements of the process limit rather narrowly the temperature range at which the process is carried out. The process is conducted at a temperature in the range of from about 15° C. to about 35° C., more preferably from about 20° C. to about 25° C. It has been determined that reaction temperatures higher than about 35° C. decomposition of the substrate, whereas temperature less than about 15° C. result in a conversion to the ketone which is unreasonably slow, particularly for large scale processes where cost is a factor. Of course, the process may be operated at lower temperatures when speed of the reaction is not a major consideration. When conducted at a temperature in the range of 15° C. to 35° C., the process is substantially complete after about 30 minutes to about 24 hours, more specifically after about one to twelve hours. It is believed that if the operator attempts to isolate the product before it has completely formed, decomposition will occur because the proposed hypochlorite intermediate is a very unstable substance.

The product of the process is easily isolated by standard conditions well known to those of ordinary skill in the art. The reaction mixture may be diluted with a solvent such as toluene and filtered into an aqueous solution of an inorganic base as defined above. A nonaqueous isolation may be utilized as well, but such isolation is preferably not so conducted. The product thus isolated may be purified if desired, but is preferably used without further isolation in subsequent reactions.

The present process has several advantages over other procedures known to oxidize alcohols to ketones. For examples, this process is extremely cost-effective and affords the desired product in high yield with ease of operation. Accordingly, the process is ideal for use in an industrial scale. Further, because of the ability to isolate the product under non-aqueous conditions, the process is particularly useful when the resulting ketone is soluble in aqueous media. Finally, because the present reaction conditions are essentially neutral, the oxidation of compounds having highly acid-labile substituents is now a possibility.

The starting materials employed in the present process are all known in the art and readily available. For example, silica gel and calcium hypochlorite are both commericially available. The starting secondary alcohol may be readily prepared by reacting 4-methoxyphenol with lithium and 2,2-dimethyl-1,3-propanediol under reflux conditions and isolating by standard procedures.

The following Examples further illustrate specific aspects of the present invention, and are intended as an additional aid to those of ordinary skill in the art in understanding the present process. The Examples are not intended to be limiting to the scope of the present process and should not be construed.

EXAMPLE 1

3,3-Dimethyl-1,5-dioxaspiro<5.5>undecan-9-one

Forty grams (0.2 mol) of 3,3-dimethyl-1,5-dioxaspiro<5.5>undecan-9-ol were dissolved in 400 ml of acetonitrile, and 23.5 g of sodium bicarbonate was added thereto with stirring. Next, 40.0 g of silica gel (MCB Grade 62 60-200 mesh) was added to the mixture, which was followed by the addition of 40.0 g (0.28 mol) of calcium hypochlorite (Fisher Chemical Company) portion-wise over a period of 90 seconds. The reaction mixture was stirred at 23.5° C. for one hour and then heated slowly to 28.5° C., and the reaction mixture was stirred overnight. The mixture was filtered into a stirring solution of 8.0 g of sodium bicarbonate in 80 ml of water. The flask was rinsed with 200 ml of toluene and the filtrate was stirred for 90 minutes. The mixture was partially evaporated under reduced pressure and 400 ml of toluene was added thereto. The organic phase was washed with 100 ml of a saturated aqueous sodium chloride solution containing 5.0 g of sodium bicarbonate. the organic phase was dried over anhydrous sodium sulfate. The volatiles were removed under reduced pressure and the residue was held under vacuum for about 60 hours. A total of 38.56 g of 3,3-dimethyl-1,5-dioxaspiro<5.5>-undecan-9-one was obtained having a purity of 93.7% by gas chromatographic analysis (97.2% crude yield). The compound was stored in a solution of 3.55 g of sodium bicarbonate in 200 ml methylene chloride in a sealed bottle.

EXAMPLE 2

3,3-Dimethyl-1,5-dioxaspiro<5.5>undecan-9-one

Three grams of silica gel (MCB 60-200 mesh) were added to a solution of 3.0 g (0.015 mol) of 3,3-dimethyl-1,5-dioxaspiro<5.5>undecan-9-ol in 30 ml of acetonitrile at 25° C. To the stirred solution was added 3.0 g of calcium hypochlorite (Fisher) and the reaction mixture was stirred at about 23°-27° C. for about 19 hours. The mixture was heated at about 30°-32° C. for 90 minutes and 29°-30° C. for two and one-half hours. The mixture was filtered and the flask was rinsed with 15 ml of toluene. The filtrate was evaporated to dryness under reduced pressure and 20 ml of toluene and 10 ml of water were added to the residue. After 45 minutes, the organic phase was separated, washed with 20 ml of a saturated sodium chloride solution and dried over anhydrous sodium sulphate. An NMR of the solution indicated the presence of 3,3-dimethyl-1,5-dioxaspiro-<5.5>undecan-9-one. Gas chromatographic anaylsis indicated the solution was 98% pure product.

EXAMPLE 3

3,3-Dimethyl-1,5-dioxaspiro<5.5>undecan-9-one

Sodium bicarbonate (8.81 g, 0.105 mol) was added to a solution of 15.0 g (0.075 mol) of 3,3-dimethyl-1,5-dioxaspiro<5.5>undecan-9-ol in 150 ml of acetonitrile. The reaction mixture was charged with 15.0 g of silica gel (MCB 60-200 mesh) and 15.0 g of calcium hypochlorite in sequence. The reaction mixture was stirred at a temperature in the range of 24° C. to 28° C. for about 18 hours and then warmed to 29° C. to 30° C. for 4 hours. The mixture was filtered and evaporated under vacuum. The residue was combined with 135 ml of toluene and 50 ml of water, and the resulting mixture was stirred for 45 minutes. The organic phase was separated, washed with 50 ml of a saturated sodium chloride solution and dried over 10.0 g of anhydrous sodium sulfate. A gas chromatograph of the sample showed 93.6% pure product. The organic phase was concentrated under vacuum to afford 13.97 g of 3,3-dimethyl-1,5-dioxaspiro<5.5>undecan-9-one.

EXAMPLE 4

3,3-Dimethyl-1,5-dioxaspiro<5.5>undecan-9-one

A mixture of 1.76 g (0.021 mol) of sodium bicarbonate, 3.0 g of silica gel (MCB, 60-200 mesh), 3.0 g of calcium hypochlorite (Fisher) and 3.0 g (0.015 mol) of 3,3-dimethyl-1,5-dioxaspiro<5.5>undecan-9-ol in 30 ml of acetonitrile was stirred at a temperature in the range of 23° C. to 30.5° C. for about 8 hours. The mixture was stirred at about 25° C. for about 60 hours. The reaction mixture was filtered and 0.55 g of sodium bicarbonate and 6 ml of water was added to the filtrate. The flask was rinsed with 15.0 ml of toluene and the filtrate was evaporated to a weight of 7.02 g under vacuum. The mixture was charged with 30 ml of toluene and 10 ml of water. The organic layer was separated, washed with 10 ml of water and dried over 1.0 g of anhydrous sodium sulfate. A gas chromatograph of the solution indicated 94.8% product.

EXAMPLE 5

3,3-Dimethyl-1,5-dioxaspiro<5.5>undecan-9-one

Forty grams (0.2 mol) of 3,3-dimethyl-1,5-dioxaspiro<5.5>undecan-9-ol was dissolved in 400 ml of acetonitrile. This solution was charged with 23.5 g (0.28 mol) of sodium bicarbonate, 40.0 g of silica gel and 40.0 g of calcium hypochlorite in sequence. The mixture was stirred at a temperature in the range of 22°-24° C. for about 6 hours, at about 17° C. for 16 hours and between 24°-30° C. for 8 hours. The mixture was stirred at about 22° C. for another 16 hours and was filtered. The filter was rinsed with 200 ml of toluene. After about 2 hours the solution had discolored and thin layer chromatography indicated that some decomposition had occurred. Five grams of sodium bicarbonate were added to the filtrate. Part of the solution was decanted and the remainder was stored until ready for subsequent use.

EXAMPLE 6

3,3-Dimethyl-1,5-dioxaspiro<5.5>undecan-9-one

Thirty milliliters of acetonitrile was added to 3.0 g (0.015 mol) of 3,3-dimethyl-1,5-dioxaspiro<5.5>-undecan-9-ol and 1.76 g (0.021 mol) of sodium bicarbonate. To this mixture was added 3.0 g of silica gel (MCB 60-200 mesh) and 3.0 g of calcium hypochlorite (Fisher). The mixture was stirred at a temperature in the range of 22° C. to 30° C. for about 24 hours and filtered into a solution of 0.6 g of sodium bicarbonate and 6 ml of water. The flask was rinsed with 15 ml of toluene. The filtrate was stirred for 75 minutes and evaporated under reduced pressure. The partially evaporated mixture was stirred for 50 minutes and 30 ml of toluene and 7.5 ml of a saturated sodium chloride solution. The layers were separated and the organic phase was dried over 1.0 g of anhydrous sodium sulfate and 0.2 g of sodium bicarbonate. A gas chromatograph of the solution indicated 96.47% product.

The compounds prepared by the present process are useful for a variety of purposes, particularly as intermediates to other organic compounds, as evidenced by the compound's commercial availability (See, e.g., Aldrich Chemical Company, Milwaukee, Wisc., Catalog/Handbook of Fine Chemicals).

The product of the present process is preferably used as an intermediate to certain octahydropyrazolo[3,4-g]quinolines. Such compounds are useful as taught, for example, by U.S. Pat. No. 4,198,415 of Kornfeld et al., as dopamine agonists useful in the treatment of Parkinsonism and in inhibiting secretion of prolactin.

The use of the compounds prepared by the present process as intermediates to octahydropyrazolo[3,4-g]quinolines is typical of the general practice of chemists, but may be illustrated by the following reaction scheme:

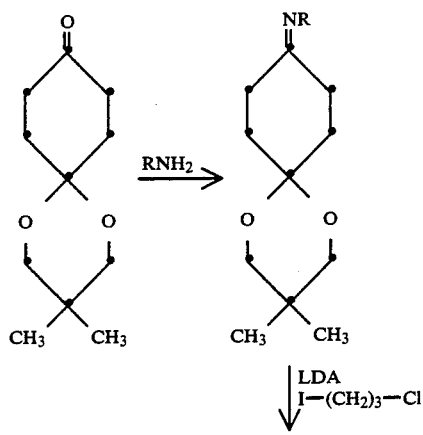

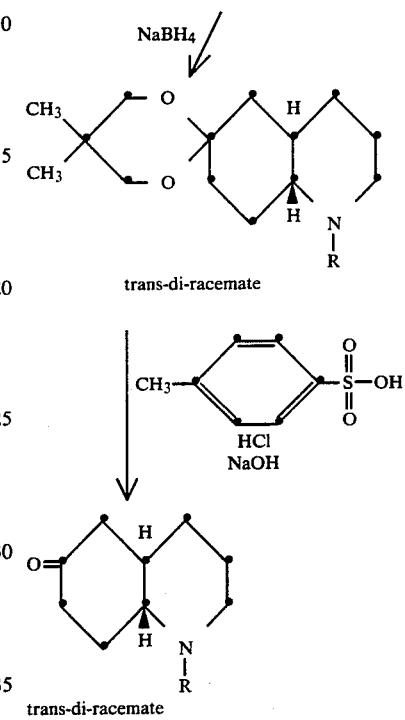

wherein R represents a $C_1$-$C_3$ alkyl group.

In the first step of the above described reaction scheme, the imine is prepared by the reaction of the ketone prepared by the present process and a primary ($C_1$-$C_3$alkyl)amine. Typically the reaction is conducted by refluxing the reactants in toluene with an acid catalyst such as p-toluenesulfonic acid. A means of removing the water formed as a by-product of the reaction is also necessary, and generally either molecular sieve, anhydrous inert inorganic salts or a DeanStark trap may be employed. The product may then be isolated simply by removing the volatiles under reduced pressure.

The preparation of the endocyclic enamine as outlined above from the corresponding imine has been outlined in general by Evans in *Journal of the American Chemical Society* 92, 7593 (1970). More specifically, this reaction involves treating the imine with lithium diisopropylamine (LDA) (prepared by the reaction of n-butyllithium with diisopropylamine) at a temperature in the range of −20° C. to about −100° C., more preferably at about −40° C. to −50° C. To this solution is added 1-chloro-3-iodopropane at a temperature in the same range as defined above. Cyclization is effected by heating the reaction mixture in the range of 50° C. to 150° C., more typically at the reflux temperature of the reaction mixture. The resulting enamine may be isolated by evaporative distillation and stored under nitrogen until used in the following reaction.

Reduction of the endocyclic enamine thus prepared to the corresponding trans-dl-racemate with sodium borohydride is generally taught by Marshall et al. the

*Journal of Organic Chemistry* in Vol. 28,421 (1963). Typically this reaction is carried out by treating the enamine with at least one mole equivalent of sodium borohydride in an alcoholic solvent such as ethanol. This process is conducted at a temperature in the range of −25° C. to 200° C., more preferably at about 0° C. to 50° C. A solution of acetic acid is finally added to the reaction mixture and the product isolated by standard procedures.

The final step in the above described process involves the conversion of the ketal to the ketone. This is conducted by standard hydrolysis procedures, preferably by treating the p-toluenesulfonate salt with concentrated hydrochloric acid.

The foregoing process is used to prepare the quinoline derivative as defined above. This compound is then converted to the corresponding biologically active octahydropyrazolo[3,4-g]quinoline according to the teaching of U.S. Pat. No. 4,198,415, herein incorporated by reference.

The following preparations illustrate the use of the product of the process of this invention.

Preparation of (8aR-trans)-octahydro-1-propyl-6(2H)-quinolinone

A. N-(3,3-Dimethyl-1,5-dioxaspiro<5.5>undec-9-ylidene)-1-propanamine

A 250 ml single neck round bottom flask fitted with a water separator containing 20 g of 3A sieves (Linde) was charged with 100 ml of toluene, 10.25 g (0.052 mol) of 3,3-dimethyl-1,5-dioxaspiro[5.5]undecan-9-one (Aldrich Chemical Company), 17.97 g (3.04 mmol) of n-propylamine (Baker) and 18 mg (0.09 mmol) of p-toluenesulfonic acid monohydrate (Alrich). The reaction mixture was refluxed for 24 hours and cooled, and the toluene was evaporated under reduced pressure to produce the title compound.

B. 1′,3′,4′,5′,7′,8′-Hexahydro-5,5-dimethyl-1′-propylspiro[1,3-dioxane-2,6′-(2′H)-quinoline]

In a separate container, 36 ml of 1.51 M (0.054 mol) n-butyllithium was added to 7.0 g (0.054 mol) of diisopropylamine in 16 ml of dry tetrahydrofuran at −25° C. under nitrogen. The stirred reaction mixture was warmed to approximately 0° C. for 30 minutes and then recooled to -60° C. with a dry ice/acetone bath. The residue containing N-(3,3-dimethyl-1,5-dioxaspiro<5.5>undec-9-ylidene)-1-propanamine prepared above was dissolved in 16 ml of tetrahydrofuran and the solution added dropwise to the −60° C. solution. The resulting reaction mixture was allowed to warm slightly and was stirred at a temperature in the range of −25° C. to −35° C. for 30 minutes. The reaction mixture was cooled to −65° C. and 11.1 g (0.054 mol) of 1-chloro-3-iodopropane was added thereto in one portion. The mixture was warmed to 25° C. over a 30 minute period and refluxed for four hours. The reaction mixture was allowed to stand overnight and the volatiles were removed under reduced pressure. The resulting residue was combined with 200 ml of ether and 5.0 g of 3A molecular sieve. The mixture was stirred for 20 minutes and filtered under nitrogen, and the solids were rinsed with two 50 ml portions of ether. The filtrate was evaporated under nitrogen to provide 15.17 g of 1,3,4,5,7,8-hexahydro-5,5-dimethyl-1′-propylspiro[1,3-dioxane-2,6′(2′H)-quinoline], which was stored under nitrogen at −25° C. A proton NMR under nitrogen of the compound verified the structure of the product.

C. (8′aR-trans)-Octahydro-5,5-dimethyl-1′-propylspiro[1,3-dioxane-2,6′(2′H)-quinoline]

The compound prepared above and stored under nitrogen at −25° C. was combined with 9.9 g of sodium borohydride and 250 ml of ethanol under nitrogen. The stirred reaction mixture was cooled to 0° C. and a solution of 18 ml of acetic acid in 50 ml of ethanol was added at such rate so as to keep the temperature of the reaction mixture below about 10° C. Due to the thickness of the reaction mixture an additional 150 ml of ethanol was added. After 3 hours the addition was complete and the reaction mixture was stirred for an additional 2 hours at 0°–5° C., and 1 hour at 25° C. The mixture was cooled to 0° C., quenched with 20 ml of acetone and allowed to warm to 25° C. over a 30 minute period. The mixture was evaporated to dryness under vacuum and the residue was combined with 500 ml of ether and 500 ml of deionized water. The solution was stirred for 1 hour and the layers were separated. Two hundred milliliters of a saturated sodium chloride solution was added to the aqueous phase, and the solution was extracted with methylene chloride. The organic phases were combined and dried with anhydrous potassium carbonate. The volatiles were evaporated under reduced pressure to afford 11.2 g of a pale yellow oil. Eleven grams of this material was chromatographed over silica gel eluting with a solvent system composed of 300 ml of methylene chloride and 500 ml each of 3%, 5%, 8%, 11% methanol in methylene chloride, and then 1 l. of 15% methanol in methylene chloride containing 0.2% concentrated ammonium hydroxide (v/v). The chromatography provided 9.1 g of (8′aR-trans)-octahydro-5,5-dimethyl-1′-propylspiro[1,3-dioxane-2,6′(2′H)-quinoline]

Analysis calculated for $C_{17}H_{31}NO_2$: Theory: C, 72.55; H, 11.10; n, 4.98; O, 11.37; Cl, 0.00. Found: C, 72.23; H, 10.92; N, 4.77; O, 11.63; Cl, 0.00.

D. (8′aR-trans)-Octahydro-5,5-dimethyl-1′-propylspiro[1,3-dioxane-2,6′(2′H)-quinoline]4-methyl-benzenesulfonate (1:1)

Eight hundred and forty-seven milligrams (4.46 mmol) of p-toluenesulfonic acid (Aldrich) dissolved in 5 ml of methanol was added to a solution of 1.163 g (4.46 mmol) of (8′aR-trans)-octahydro-5,5-dimethyl-1′-propylspiro[1,3-dioxane-2,6′(2′H)-quinoline] in 5 ml of methanol. The reaction mixture was stirred at 25° C. and evaporated to dryness under reduced pressure. The residue was combined with 10 ml of toluene and the solution again evaporated under reduced pressure. This procedure was repeated twice. Fifteen milliliters of toluene was added to the residue and the solution was cooled to 0° C. The precipitated solid was collected by filtration to afford 558 mg of (8′aR-trans)-octahydro-5,5-dimethyl-1′-propylspiro[1,3-dioxane-2,6′(2′H)-quinoline] 4-methylbenzenesulfonate (1:1). mp=164°–169° C. An NMR of the solid confirmed the structure of the product.

Analysis calculated for $C_{17}H_{31}NO_2$: Theory: C, 63,54; H, 8.67; N, 3.09; O, 17.63; S, 7.07. Found: C, 63.77; H, 8.43; N, 2.89; O, 17.72; S, 6.88.

E. A 20 ml via was charged with 558 mg (1.23 mmol) of (8′aR-trans)-octahydro-5,5-dimethyl-1′-propylspiro[1,3-dioxane-2,6′(2′H)-quinoline] 4-methylbenzenesulfonate (1:1), 1.2 ml of tetrahydrofuran, 0.9 ml of water and 0.25 ml (3 mmol) of concentrated hydrochloric acid. The reaction mixture was stirred at 25° C. for 14 hours and 10 ml of water was added thereto. The aqueous solution was washed with methylene chloride and neutralized with sodium bicarbonate. The pH of the neutralized aqueous solution was raised to 12 with 1N sodium hydroxide and the resulting solution was twice extracted with ethyl acetate. The organic phase was dried over anhydrous sodium sulfate and evaporated to dryness under reduced pressure. The residue was purified over silica gel eluting with a 250:12.5:1.25 chloroform:methanol:ammonium hydroxide (v/v/v) solvent system to afford (8aR-trans)-octahydro-1-propyl-6(2H)-quinoline. The product thus isolated was identical to an authentic reference sample by thin layer chromatography in the solvent system described above.

We claim:

1. A compound of the formula

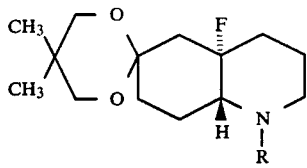

wherein R is $C_1$–$C_3$ alkyl.

* * * * *

UNITED STATES PATENT AND TRADEMARK OFFICE
CERTIFICATE OF CORRECTION

PATENT NO. : 4,689,415
DATED : August 25, 1987
INVENTOR(S) : Randall K. Atkins and Leland O. Weigel It is certified that error appears in the above—identified patent and that said Letters Patent is hereby corrected as shown below:

Column 10, lines 4-8, in Claim 1, the part of the structure which reads

" 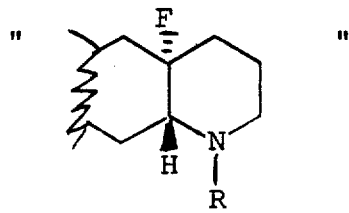 "

should read

-- 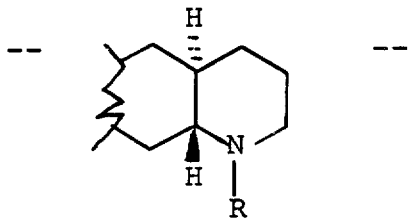 --

Signed and Sealed this

Second Day of February, 1988

*Attest:*

DONALD J. QUIGG

*Attesting Officer*  *Commissioner of Patents and Trademarks*